United States Patent [19]

Modena et al.

[11] Patent Number: 4,810,765

[45] Date of Patent: Mar. 7, 1989

[54] COTELOMERS OF VINILYDENE FLUORIDE WITH FLUORINATED OLEFINS AND PROCESS FOR THEIR PREPARATION

[75] Inventors: Silvana Modena, Monza; Alberto Fontana, Milan; Giovanni Moggi, Milan; Gianangelo Bargigia, Milan, all of Italy

[73] Assignee: Ausimont S.p.A., Milan, Italy

[21] Appl. No.: 67,149

[22] Filed: Jun. 29, 1987

[30] Foreign Application Priority Data

Jun. 30, 1986 [IT] Italy ................... 20972 A/86

[51] Int. Cl.$^4$ ............................................. C08F 12/20
[52] U.S. Cl. .................................................. 526/249
[58] Field of Search .......................................... 526/249

[56] References Cited

U.S. PATENT DOCUMENTS

| | | | |
|---|---|---|---|
| 3,979,469 | 9/1976 | Jager ................................ | 560/192 |
| 4,002,810 | 1/1977 | Haszeldine et al. ............. | 525/359.6 |
| 4,158,678 | 6/1979 | Tatemoto et al. ................ | 522/141 |

FOREIGN PATENT DOCUMENTS

| | | | |
|---|---|---|---|
| 930757 | 7/1963 | United Kingdom ............... | 526/249 |
| 1242362 | 8/1971 | United Kingdom ............... | 526/249 |

Primary Examiner—Joseph L. Schofer
Assistant Examiner—N. Sarofim
Attorney, Agent, or Firm—Stevens, Davis, Miller & Mosher

[57] ABSTRACT

Cotelomers of vinylidene fluoride with one or more fluoro olefins, having the general formula $$R[(CF_2CH_2)_n (C_3F_6)_m (C_2F_4)_p (C_2F_3Cl)_q]X \qquad (I)$$

wherein:

X is either Br or I, R is an alkyl radical eventually containing halogen atoms, n is an integer comprised within the range of from 1 to 30, m is an integer comprised within the range of from 0 to 10, p and q are integers comprised within the range of from 0 to 20, and wherein $m+p+q$ is at least 1, obtained by cotelomerizing monomers in the presence of a telogen RX (wherein R and X have the abovesaid meaning) and of a free-radical polymerization initiator.

7 Claims, No Drawings

COTELOMERS OF VINILYDENE FLUORIDE WITH FLUORINATED OLEFINS AND PROCESS FOR THEIR PREPARATION

FIELD OF THE INVENTION

The present invention relates to cotelomers of vinylidene fluoride with fluorinated olefins containing at least one terminal bromine or iodine atom, useful as plasticizing additive in fluoroelastomeric compositions, which are peroxy-curable.

BACKGROUND OF THE INVENTION

In the technical literature processes are known for preparing homotelomers of $CH_2=CF_2$ by the action of telogen agents. Also known are copolymers of $CF_2=CH_2$ with fluorinated olefins, obtained in the presence of halogenated telogen agents (Jap. 73-96684 and 84-20310). In the known processes, said telogens, which behave as chain transfer agents, are used in amounts not higher than 1% by mol relatively to the total monomer mols. Thus, polymeric products are obtained, which have a molecular weight not lower than 8000.

THE PRESENT INVENTION

The object of the present invention is the preparation of cotelomers of vinylidene fluoride with at least one further fluorinated olefin, carried out by using free-radical polymerization initiators and a telogen agent belonging to the class of bromoalkanes and iodoalkanes, in an amount at least equal to 10% by mol relatively to the total monomer mols; the telogen can be also used in high amounts, e.g. of 100%. In these cases, the telogen is also used as the solvent medium.

The so-obtained telomers are novel products having the general formula:

$$R[(CF_2CH_2)_n(C_3F_6)_m(C_2F_4)_p(C_2F_3Cl)_q]X \qquad (I)$$

wherein X is either Br or I, the units with n, m, p, q indices are randomly distributed along the telomer chain, R is a linear or branched $C_1$–$C_{20}$ alkyl radical which can also contain halogens and also ester or ether groups, and wherein:

n is an integer comprised within the range of from 1 to 30, m is an integer comprised within the range of from 0 to 10, p and q are integers comprised within the range of from 0 to 20, with the proviso that $m+p+q$ is at least 1.

Obviously, the telomerization product can be practically constituted also by a mixture of individual cotelomers having different n, m, p, q indices (in the examples, the average values are reported).

These products find an interesting use as additives in fluoroelastomeric peroxy-curable compositions due to their action as plasticizers and to the improvement of the low-temperature properties of the cured article, and to their property of co-vulcanizing with the base fluoroelastomer in the presence of a curing agent of peroxidic type. Furthermore, they are useful for improving compatibility of fluoroelastomers with non-fluorinated elastomers.

The preparation of the cotelomers according to the invention is carried out by reacting vinylidene fluoride with one or more of the fluorinated olefins indicated in the general formula (I) in the presence of a free-radical polymerization initiator and of a telogen having the general formula RX, wherein X is either Br or I, and R is a radical belonging to the type as indicated in the general formula (I), at a temperature comprised within the range of from 0° to 200° C. The telomerization is carried out in a liquid phase, constituted by the telogen, containing the monomers, in the presence, or not, of an inert solvent.

As suitable telogens, there can be used: dibromodifluoromethane, 1,2-dibromotetrafluoroethane, trifluoromethyl iodide, bromotrichloromethane, 1-bromo-perfluorobutane, 2-bromo-propane, ter-butyl bromide.

As free-radical initiators, all those are suitable, which are well-known in the free-radical polymerization, such as the peroxides and azo-compounds. Among the peroxides, in particular, di-ter-butylperoxide, benzoylperoxide, di-cumylperoxide, bis-peroxycarbamates, bis-peroxy-carbonates, and so forth, are preferred.

The amount of free-radical initiator relatively to the total sum of fluorinated olefins is comprised within the range of from 0.01% by mol to 10%, preferably of from 1% to 5%.

As examples of cotelomers according to the invention, those can be mentioned, which have the composition, as referred only to the telomerized olefins:

$CH_2=CF_2$: from 10% to 90% by mol;
$C_3F_6$: from 0 to 45% by mol;
$C_2F_4$: from 0 to 90% by mol;
$CClF=CF_2$: from 0 to 90% by mol.

The telomers having composition:

$CH_2=CF_2$: from 50% to 90% by mol;
$C_3F_6$: from 0 to 25% by mol;
$C_2F_4$: from 10 to 50% by mol;
$CClF=CF_2$: from 10 to 50% by mol are preferred.

Any person skilled in the art will be able to select the operating conditions for obtaining the cotelomer having the desired composition.

For example, for obtaining a cotelomer having an average number molecular weight 1000, with the composition, as % by mol, of:

VDF=75; TFE=25 the process is carried out in the presence of peroxides with a VDF/TFE molar ratio of 72/28, at a temperature of 140° C., and with a telogen/monomers ratio=0.3 (telogen=$CF_2Br—CF_2Br$), by interrupting the reaction when the conversion rate has reached 30%.

The cotelomers of the invention have demonstrated to be endowed with a higher thermal stability than the corresponding $CF_2=CH_2$ homotelomers. Furthermore, contrary to what one could suppose, they have a very low $T_g$, practically of the same order as of a $CF_2=CH_2$ homotelomer having the same molecular weight.

To the purpose of illustrating the process and the products according to the invention, there are reported characteristics of $CF_2=CH_2/C_2F_4$ (VDF/TFE) cotelomers, obtained at 150° C. with 10 mol % of $CF_2Br—CF_2Br$ telogen, during a 3-hour reaction time (to comparative purposes, also the characteristics of a VDF homotelomer are shown).

| Composition, Monomers in Reaction | Composition, Monomers in Product | Polymerization Degree n + p | $T_g$ |
| --- | --- | --- | --- |
| VDF = 100% | 100% | 12 | −85° C. |
| VDF = 100% | 100% | 16 | −80° C. |
| VDF/TFE = 90/10 | 85/15 | 16 | −84° C. |
| VDF = 100% | 100% | 20 | −72° C. |
| VDF/TFE = 70/30 | 73/27 | 21 | −83° C. |

Such a result as reported in the above table is at all unexpected, because the introduction of the perfluorinated TFE, should lead to a further $T_g$ increase, due to the increased chain rigidity, as it is observed in $CH_2=CF_2$ copolymers.

For example in the case of Tecnoflon NM copolymer having the following composition: $CH_2=CF_2$ 80%, $C_3F_6$ 20% a $T_g=23°$ C. is observed, while in Tecnoflon T terpolymer having composition $CH_2=CF_2$ 62%, $C_3F_6$ 20%, TFE 18%, the Tg increases to $-17°$ C. The introduction in polymer chain of TFE units in an amount of 18% leads to an increase of $T_g=+6°$ C. (Bonardelli, Moggi, Turturro Polymer 1986 vol. 27, page 905). In the copolymers of the present invention it is not observed such a Tg increase (see Examples 2 and 2A).

The use of these cotelomers is well described in a copending Italian Patent Application No. 20973A/86 filed concurrently herewith of the same assignee.

To illustrative purposes, the following examples of practical embodiments of the invention are reported.

EXAMPLE 1

Into an AISI-316, 500-ml autoclave, 220.5 g of $CF_2Br-CF_2Br$ and 0.5 g of di-ter-butylperoxide are charged. 8.3 g of VDF and 6.0 g of PFP ($C_3F_6$) are then charged. The temperature is brought under stirring for 3 hours to 150° C., and the mass is allowed to react. The autoclave is cooled to room temperature. The $CF_2Br-CF_2Br$ excess is removed by distillation. The remaining product was characterized by N.M.R. spectrometry and elemental analysis; its osmometric average number molecular weight ($M_n$), average composition and glass transition temperature ($T_g$) were determined.

The results obtained are:
Br=24% by weight; $M_n=660$; n=4.2; m=0.8; $T_g=-94°$ C.; $C_3F_6\%=16\%$ by mol.

EXAMPLE 2

The preparation is carried out by operating according to the working conditions of Example 1, but at 140° C., using 363.3 g of $CF_2Br-CF_2Br$, 0.82 g of di-tert.butylperoxide, 12.8 g of VDF, 8.3 g of PFP and 2.5 g of TFE.

The results obtained are:
Br=21% by weight; $M_n=730$; the average values of n and m are: n=4.5, m=1.1, p=1.2, $T_g=-92°$ C.:

EXAMPLE 2A

Operating according to the same working conditions, but with 14.4 g of VDF, 8.3 g of PFP and in complete absence of TFE; a polymer having $T_g=-90°$ C. is obtained.

EXAMPLE 3

The preparation is carried out by operating according to the working conditions of Example 1, but at 140° C., using TFE instead of PFP. To the autoclave 428.4 g of $CF_2Br-CF_2Br$, 19.3 g of di-tert.butylperoxide, 19.2 g of VDF, and 3 g of TFE were charged.

The results obtained are:
Br=22.9% by weight; $M_n=690$; n=5; p=1; $T_g=-102°$ C.

EXAMPLE 4

The preparation is carried out by operating according to the modalities of Example 3, using 0.96 g of di-tert.butylperoxide, and by interrupting the test after 2 hours.

The results obtained are:
Br=21.1% by weight, $M_n=730$, n=5.8; p=1.1, $T_g=-106°$ C.

EXAMPLE 5

The preparation is carried out by operating according to the working conditions of Example 1, but at T=145° C., by using 102 g of $CF_2Br-CF_2Br$, 1.14 g of di-tert.butylperoxide, 19.2 g of VDF and 13.5 g of PFP.

The results obtained are:
$M_n=940$; n=5.8; m=2.1; $T_g=-92°$ C.

EXAMPLE 6

The preparation is carried out by operating according to the working conditions of Example 1, using 16.8 g of $CF_2Br-CF_2Br$, 1.30 g of di-tert.butylperoxide, 32 g of VDF and 22.5 of PFP.

The results obtained are:
Br=5.1% by weight, $M_n=3100$, n=28, m=7.1, $T_g=-30°$ C.

EXAMPLE 7

The preparation is carried out by operating according to the working conditions of Example 6, using 5.25 g of PFP.

The results obtained are:
$M_n=2900$; n=27; m=2.5, $T_g=-94°$ C.

EXAMPLE 8

The preparation is carried out by operating according to the modalities of Example 6, using 50.7 g of $CF_2Br-CF_2Br$.

The results obtained are:
$M_n=1200$, n=11.2, m=2.1, $T_g=-74°$ C.

EXAMPLE 9

The preparation is carried out by operating according to the working conditions of Example 4, using 85.8 g of $CF_2Br-CF_2Br$.

The results obtained are:
$M_n=900$, n=7.4, p=1.2, $T_g=-109°$ C.

EXAMPLE 10

The preparation is carried out by operating according to the working conditions of Example 9, using 25.7 g of $CF_2Br-CF_2Br$.

The results obtained are:
$M_n=950$, n=8.9; p=1.1, $T_g=100°$ C.

EXAMPLE 11

The preparation is carried out by operating as in Example 3, using 30.4 g of $CF_2Br-CF_2Br$, 20 g of VDF and 9 g of $C_2F_4$, 1.1 g of di-ter-butylperoxide. The reaction mass is heated 1 hour at 130° C.

The product obtained has an average number molecular weight ($M_n$), measured by osmometry, of 1,400. $T_g=-90°$ C.

EXAMPLE 12

The preparation is carried out by operating as in Example 1, but with 101.5 g of CF$_2$Br—CF$_2$Br, using as the peroxidic initiator Perkadox 16 (di-4,4'-tert-butyl-cyclohexyl-peroxydicarbonate) 2.7 g, charging 19.2 g of VDF and 9 g of TFE. The reaction mass has been heated for 2 hours at 62° C.

The results obtained are:

$M_n = 1.300$, $n = 11.2$, $p = 3.1$, $T_g = -86°$ C.

EXAMPLE 13

Into the apparatus as described in Example 6, 20.4 g of CF$_2$Br—CF$_2$Br, 0.9 g of di-tert-butylperoxide, 7 g of chlorotrifluotoethylene and 13 g of vinylidene fluoride are charged. The temperature is increased to 130° C. and has been maintained at this value for 150 minutes. The product is separated as described in Example 1. The average number molecular weight ($M_n$) results equal to 1,200, $n = 10.1$, $q = 3$, $T_g = -65°$ C.

What we claim is:

1. Cotelomers of vinylidene fluoride with fluorinated olefins, having the general formula:

$$R-(CF_2CH_2)_n(C_3F_6)_m(C_2F_4)_p(C_2F_3Cl)_q-Br \quad (I)$$

the units with n, m, p, q, indices are randomly distributed along the telomer chain, R is a linear or branched C$_1$–C$_{20}$ alkyl radical which may also contain halogens and ester or ether groups, and wherein:

n is an integer ranging from 1 to 30,
m is an integer ranging from 0 to 10,
p and q are integers ranging from 0 to 20, with the proviso that m+p+q is at least 1.

2. Process for the preparation of the cotelomers of claim 1, comprising reacting vinylidene fluoride with one or more fluorinated olefins as indicated in formula (I) in the presence of a free radical polymerization initiator and of a telogen having the general formula RBr, wherein R is a radical having the same meaning as specified in claim 1, the reaction temperature being from 0° to 200° C.

3. Cotelomers according to claim 1, wherein the composition, as referred to the telomerized olefins only, is as follows:

CH$_2$=CF$_2$: from 10% to 90% by mol;
C$_3$F$_6$: from 0 to 45% by mol;
C$_2$F$_4$: from 0 to 90% by mol;
CClF=CF$_2$: from 0 to 90% by mol.

4. Cotelomers according to claim 3, wherein the composition is as follows:

CH$_2$=CF$_2$: from 50% to 90% by mol;
C$_3$F$_6$: from 0 to 25% by mol;
C$_2$F$_4$ and C$_2$F$_3$Cl: from 10 to 50% by mol.

5. Process according to claim 2, wherein the telogen is at least in an amount of 10%.

6. Process according to claim 2, wherein the free-radical initiator is comprised in amount within the range of from 0.01% to 10% by mol, referring to the total sum of the olefins to be polymerized.

7. Process according to claim 2, wherein the free radical initiator is comprised in amount within the range of from 1% to 5%.

* * * * *